(12) United States Patent
Riobo Aboy

(10) Patent No.: US 7,927,283 B2
(45) Date of Patent: Apr. 19, 2011

(54) BLOOD PRESSURE ALGORITHM

(75) Inventor: Pedro Mateo Riobo Aboy, Beaverton, OR (US)

(73) Assignee: Tiba Medical, Inc., Portland, OR (US)

( * ) Notice: Subject to any disclaimer, the term of this patent is extended or adjusted under 35 U.S.C. 154(b) by 147 days.

(21) Appl. No.: 12/052,659

(22) Filed: Mar. 20, 2008

(65) Prior Publication Data

US 2008/0234589 A1 Sep. 25, 2008

Related U.S. Application Data

(60) Provisional application No. 60/895,902, filed on Mar. 20, 2007.

(51) Int. Cl.
*A61B 5/02* (2006.01)

(52) U.S. Cl. .................................... 600/490; 600/500

(58) Field of Classification Search .................. 600/485, 600/490, 493–496
See application file for complete search history.

(56) References Cited

U.S. PATENT DOCUMENTS

| | | | |
|---|---|---|---|
| 4,154,238 A | 5/1979 | Link | |
| 4,984,577 A | 1/1991 | Frankenreiter | |
| 5,054,494 A | 10/1991 | Lazzaro et al. | |
| 5,170,795 A | 12/1992 | Ramsey, III et al. | |
| 5,267,567 A | 12/1993 | Aung et al. | |
| 5,577,508 A | 11/1996 | Medero | |
| 5,579,776 A | 12/1996 | Medero | |
| 5,590,662 A | 1/1997 | Hersh et al. | |
| 5,680,870 A | 10/1997 | Hood, Jr. et al. | |
| 5,687,731 A | 11/1997 | Ragozin et al. | |
| 5,704,362 A | 1/1998 | Hersh et al. | |
| 5,865,756 A | 2/1999 | Peel, III | |
| 6,440,080 B1 | 8/2002 | Booth et al. | |
| 6,443,905 B1 * | 9/2002 | Nissila et al. | 600/490 |
| 6,719,703 B2 | 4/2004 | Chen et al. | |
| 6,808,496 B2 | 10/2004 | Oka et al. | |
| 7,014,611 B1 | 3/2006 | Geddes et al. | |
| 2001/0049476 A1 | 12/2001 | Forstner | |
| 2002/0082507 A1 | 6/2002 | Kolluri et al. | |
| 2003/0069507 A1 | 4/2003 | Nishibayashi | |
| 2003/0092999 A1 | 5/2003 | Goto et al. | |
| 2003/0097074 A1 | 5/2003 | Koa et al. | |
| 2003/0199776 A1 | 10/2003 | Narimatsu et al. | |
| 2003/0208127 A1 | 11/2003 | Archibald et al. | |
| 2004/0111033 A1 | 6/2004 | Oung et al. | |
| 2004/0147848 A1 | 7/2004 | Shirasaki et al. | |
| 2004/0167411 A1 | 8/2004 | Kolluri et al. | |
| 2005/0148885 A1 | 7/2005 | Tweed et al. | |

(Continued)

OTHER PUBLICATIONS

A Novel Algorithm to Estimate the Pulse Pressure Variation Index, Mateo Aboy Et al, IEEE Transactions on Niomedical Engineering, vol. 51, No. 12, Dec. 2004.*

(Continued)

*Primary Examiner* — Charles A Marmor, II
*Assistant Examiner* — Michael D'Angelo
(74) *Attorney, Agent, or Firm* — Mateo Aboy; Aboy & Associates, PC

(57) ABSTRACT

A apparatus and method for non-invasively measuring blood pressure. Cuff pressure and oscillometric signals are generated. The signals are conditioned by a plurality of linear filters to remove artifacts and local trends. Rank-order filters are applied to the conditioned oscillometric signal to detect upper and lower envelops. The systolic blood pressure and diastolic blood pressure are calculated using a plurality of multidimensional threshold vectors.

9 Claims, 10 Drawing Sheets

U.S. PATENT DOCUMENTS

| | | | |
|---|---|---|---|
| 2005/0187483 A1 | 8/2005 | Kolluri et al. | |
| 2005/0234350 A1 | 10/2005 | Sawanoi et al. | |
| 2006/0116588 A1 | 6/2006 | Archibald et al. | |
| 2006/0224068 A1 | 10/2006 | Nunome | |
| 2006/0253040 A1* | 11/2006 | Stergiopoulos et al. | 600/493 |
| 2007/0106163 A1 | 5/2007 | Friedman et al. | |
| 2007/0118036 A1* | 5/2007 | Hersh et al. | 600/485 |
| 2007/0142730 A1 | 6/2007 | Laermer et al. | |
| 2007/0142731 A1 | 6/2007 | Ye et al. | |
| 2007/0185401 A1 | 8/2007 | Quinn et al. | |
| 2007/0232939 A1 | 10/2007 | Forstner | |
| 2008/0064968 A1 | 3/2008 | Martin et al. | |

OTHER PUBLICATIONS

Gert A. Van Montfrans; "Oscillometric blood pressure measurement: progress and problems"; Blood Pressure Monitoring 2001, 6:287-290; the Netherlands.

John N. Amoore; Extracting oscillometric pulses from the cuff pressure: does it affect the pressures determined by oscillometric blood pressure monitors?; Blood Pressure Monit.

JCTB Moraes, M. Cerulli; A Strategy for Determination of Systolic, Mean and Diastolic Blood Pressures from Oscillometric Pulse Profiles; Computers in Cadiology 2000, 27: 211-2.

Masaru Sugimachi et al; "Faster Oscillometric manometry does not sacrifice the accuracy of blood pressure deterrmination"; Blood Pressure Monitoring 2004, 9: 135-141; Japan.

M. A. Kaufmann; "Oscillometric Blood Pressure Measurements by Different Devices Are Not Interchangeable"; Anesth Analg 1996, 82: 377-381; Boston.

JCTB Moraes, M. Cerulli; "Development of a New Oscillometric Blood Pressure Measurement System"; Computers in Cardiology 1999, 26: 467-470; Brazil.

A. Ball-Ilovera et al; "An Experience in Implementing the Oscillometric Algorithm for the Non-Invasive Determination of Human Blood Pressure"; Proceedings of the 25th Annual I.

* cited by examiner

US 7,927,283 B2

BLOOD PRESSURE ALGORITHM

CROSS-REFERENCE

This application claims the benefit of U.S. Provisional Patent Application No. 60/895,902 filed on 2007-03-20 by the present inventors, which is incorporated by reference.

BACKGROUND OF THE INVENTION

1. Field of the Invention

The present invention relates to automated noninvasive blood pressure monitoring. Specifically, it relates to methods, systems, and apparatuses for calculating noninvasive blood pressure and associated clinical parameters which employ the oscillometric method and automatic heart rate calculation.

2. Description of the Related Art

Various techniques have been proposed for noninvasive measurement of blood pressure. A technique employed by many commercial monitoring systems is based on the well-known "oscillometric" method. The oscillometric technique requires measuring the pulsations induced by the artery as the cuff is inflated and deflated. As the cuff inflates to a predetermined pressure above the systolic blood pressure, the artery of the arm is compressed and the passage of the blood is stopped. At this point no oscillometric pulsation is sensed by the device. Then, the cuff is gradually deflated and the oscillations become increasingly significant until the pulse pressure in these oscillations reaches a maximum amplitude. The point at which the oscillations have a maximum amplitude corresponds to the mean arterial pressure (MAP) on the cuff pressure signal. Systolic blood pressure (SBP) and diastolic blood pressure (DBP) are then calculated empirically based on the MAP as two different percentage points before and after the MAP point. Numerous blood pressure measurement-related inventions have been proposed based on the underlying principle of the oscillometric technique such as U.S. Pat. Nos. 4,984,577, 7,300,404, 7,153,269, 7,041,060, 7,052,465, 7,118,535, 7,311,669, and many others. Prior-art references of the oscillometric technique typically rely on performing some type of beat detection in order to calculate the pulse pressure in the oscillometric signal and determine the heart rate, and rely on two fixed MAP-based thresholds to determine SBP and DBP. Improved methods can be obtained by eliminating the need for automatic detection algorithms and by incorporating vector-based thresholds that increase the accuracy of the blood pressure measurement system. Additionally, improvements on the basic oscillometric method can be made in order to increase the robustness to motion artifact.

BRIEF DESCRIPTION OF THE SEVERAL VIEWS OF THE DRAWING(S)

DETAILED DESCRIPTION OF THE INVENTION

Figure 1:
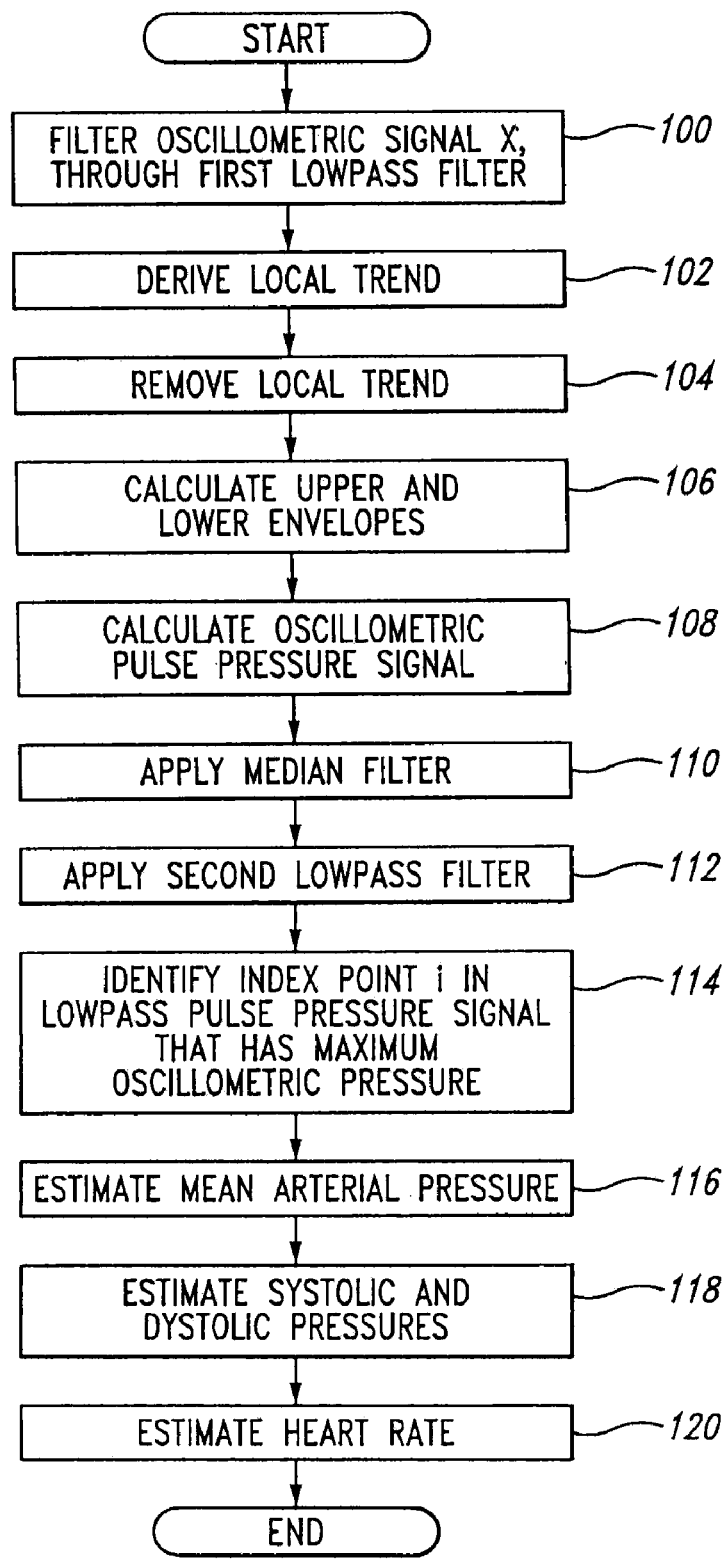
FIG. 1 shows a flow chart of a method for a non-invasive measurement of blood pressure.

FIG. 1 shows a flow chart of a method for a non-invasive measurement of blood pressure. The method uses as input a oscillometric signal $x_1$ and a cuff pressure signal $x_2$. This method is accomplished by filtering the oscillometric signal $x_1$ using linear filters to remove artifacts, calculating the pulse pressure envelope without beat detection by using rank-order filters, and determining the heart rate based on a spectrum analysis of the oscillometric signal $x_1$.

Step 100 comprises filtering the oscillometric signal $x_1$ with a first lowpass filter to remove high frequency noise and artifacts. The result is a lowpass filtered oscillometric signal $x_1^l$. This step is performed in accordance with Equation (1):

$$x_1^l(n) = x_1(n) * h_l(n) = \sum_{k=0}^{M_l} h_l(n) x_1(n-k) \tag{1}$$

where $M_l$ denotes a first lowpass filter order, $h_l(n)$ denotes a first lowpass filter impulse response and n denotes a sample index. The first lowpass filter order $M_l$ and first lowpass filter impulse response $h_l(n)$ are determined based on a selected patient population and selected measuring conditions. In some embodiments, the first lowpass filter order $M_l$ and first lowpass filter impulse response $h_l(n)$ are selected to meet a criteria of removing anticipated noise and artifacts when filtering oscillometric signals from a particular patient population under a particular set of environmental conditions.

Step 102 comprises deriving a local trend signal $x_1^t$ from the lowpass filtered oscillometric signal $x_1^l$ using a local trend filter. This step is performed in accordance with Equation (2):

$$x_1^t(n) = x_1^l(n) * h_t(n) = \sum_{k=0}^{M_t} h_t(n) x_1^l(n-k) \tag{2}$$

where $M_t$ denotes an order of the local trend filter, $h_t(n)$ denotes the impulse response of the local trend filter and n denotes the sample index. The local trend filter order $M_t$ and the local trend filter impulse response $h_t(n)$ are determined based on the selected patient population and selected measuring conditions.

Step 104 comprises removing the local trend signal $x_1^t$ from the lowpass filtered oscillometric signal $x_1^l$. The result is a detrended lowpass filtered oscillometric signal $x_1^h$. This step is performed in accordance with Equation (3):

$$x_1^h(n) = x_1^l(n) - x_1^t(n) = \sum_{k=0}^{M_l} h_l(n) x_1(n-k) - \sum_{k=0}^{M_t} h_t(n) x_1^l(n-k) \tag{3}$$

Step 106 comprises calculating the upper and lower envelope signals of the detrended lowpass filtered oscillometric signal $x_1^h(n)$ using a rank-order filter. This step is performed in accordance with Equation (4):

$$(u(n),l(n))=\Pi\{x_1^h(n),w_l,u_p,l_p\} \quad (4)$$

where $u(n)$ and $l(n)$ denote the upper and lower envelope signal, respectively, $w_l$ denotes the window length (i.e. number of samples use to calculate the percentiles), $u_p$ represents the upper percentile, and $l_p$ represents the lower percentiles (configurable).

Step 108 comprises calculating the oscillometric pulse pressure signal $p_p(n)$ by subtracting the lower envelope signal from the upper envelope signal. This step is performed in accordance with Equation (5):

$$p_p(n)=u(n)-l(n) \quad (5)$$

In some embodiments, steps 106 and 108 are combined to save memory. That is, the intermediate results of step 106 are not stored in memory, but used immediately in step 108 to calculate the oscillometric pulse pressure signal $p_p(n)$ which is subsequently stored in memory.

Step 110 comprises applying a median filter to the pulse pressure signal $p_p(n)$ to remove components due to artifact. The result is a median filtered pulse pressure signal $p_p^m(n)$. This step is performed in accordance with Equation (6):

$$p_p^m = \Pi\{p_p(n), w_l^m\} \quad (6)$$

where the median filter window $w_l^m$ is determined based on the selected patient population and selected measuring conditions.

Step 112 comprises applying a second lowpass filter to the median filtered pulse pressure signal $p_p^m(n)$ to remove high frequency components due to artifact. The result is a lowpass pulse pressure signal $p_p^l(n)$. This step is performed in accordance with Equation (7):

$$p_p^l(n) = p_p^m(n) * h_p(n) = \sum_{k=0}^{M_p} h_p(n) p_p^m(n-k) \quad (7)$$

where $M_p$ denotes a second lowpass filter order and $h_p(n)$ denotes a second lowpass filter impulse response. The second lowpass filter order $M_p$ and the second lowpass filter impulse response $h_p(n)$ are determined based on the selected patient population and selected measuring conditions.

Step 114 comprises identifying an index point i in the lowpass pulse pressure signal $p_p^l(n)$ that has a maximum oscillometric pulse pressure. This step is performed in accordance with Equation (8):

$$i = \arg\max_{0 \le n \le L} \{p_p^l(n)\} \quad (8)$$

Step 116 comprises estimating mean arterial pressure m by finding the cuff pressure at maximum pulse pressure index point i. This step is performed in accordance with Equation (8):

$$m = x_2(i) \quad (9)$$

Step 118 comprises estimating the systolic s, and diastolic d, pressures. This is done by identifying index points $t_s$ and $t_d$. Index points $t_s$ and $t_d$ are percent points preceding and following maximum pulse pressure index point i in the lowpass pulse pressure signal $p_p^l(n)$. The systolic s, and diastolic d, pressures are estimated by identifying index points $t_s$ and $t_d$ in the cuff pressure signal $x_2(n)$. In some embodiments, index points $t_s$ and $t_d$ are two vectors or matrices defined as a function of the patient population and conditions such as mean arterial pressure, arm circumference, and heart rate.

Step 120 comprises estimating a heart rate $f_c$ (cardiac frequency) by finding a frequency corresponding to a maximum spectrum amplitude in a range of physiologic interest. This step is done in accordance with Equation 10:

$$f_c = \arg\max_{f_l \le f \le f_h} \frac{1}{N} \left| \sum_{n=-\infty}^{\infty} x_k(n) w_R(n) e^{-j2\pi f n} \right| \quad (10)$$

$$\approx \arg\max_{f_l \le f \le f_h} |FFT\{x_w^h(n), N\}|$$

where by default $x_w^h(n) = x_1^h(i - \alpha f_s : i + \alpha f_s)$, that is, a $2\alpha$ second window of the detrended lowpass filtered oscillometric signal $x_1^h$ centered around the maximum pulse pressure index point i, and N denotes the maximum N-point Fast Fourier Transform (FFT) can be computed.

The description of the embodiment above does not represent a step-by-step sequence. The operations and methods detailed may be applied following a different sequence. The method can be implemented in hardware and firmware to make a blood pressure monitor and in software as part of a program to analyze oscillometric signals in order to measure blood pressure.

Estimating the oscillometric envelope without performing beat detection by using rank-order filters improves the robustness to motion artifact and makes the oscillometric technique more reliable. The threshold vectors can easily be generalized to multiple dimensions by including the dependence on the arm-circumference, heart rate, and other parameters. Since the dependence of the thresholds on the MAP, arm-circumference, and heart rate is conditioned on the hardware used to obtain the oscillometric and cuff pressure signals, the determination of these thresholds must be performed using a systematic optimization study where the performance of the method is monitored as these parameters are linearly varied.

Figure 2:
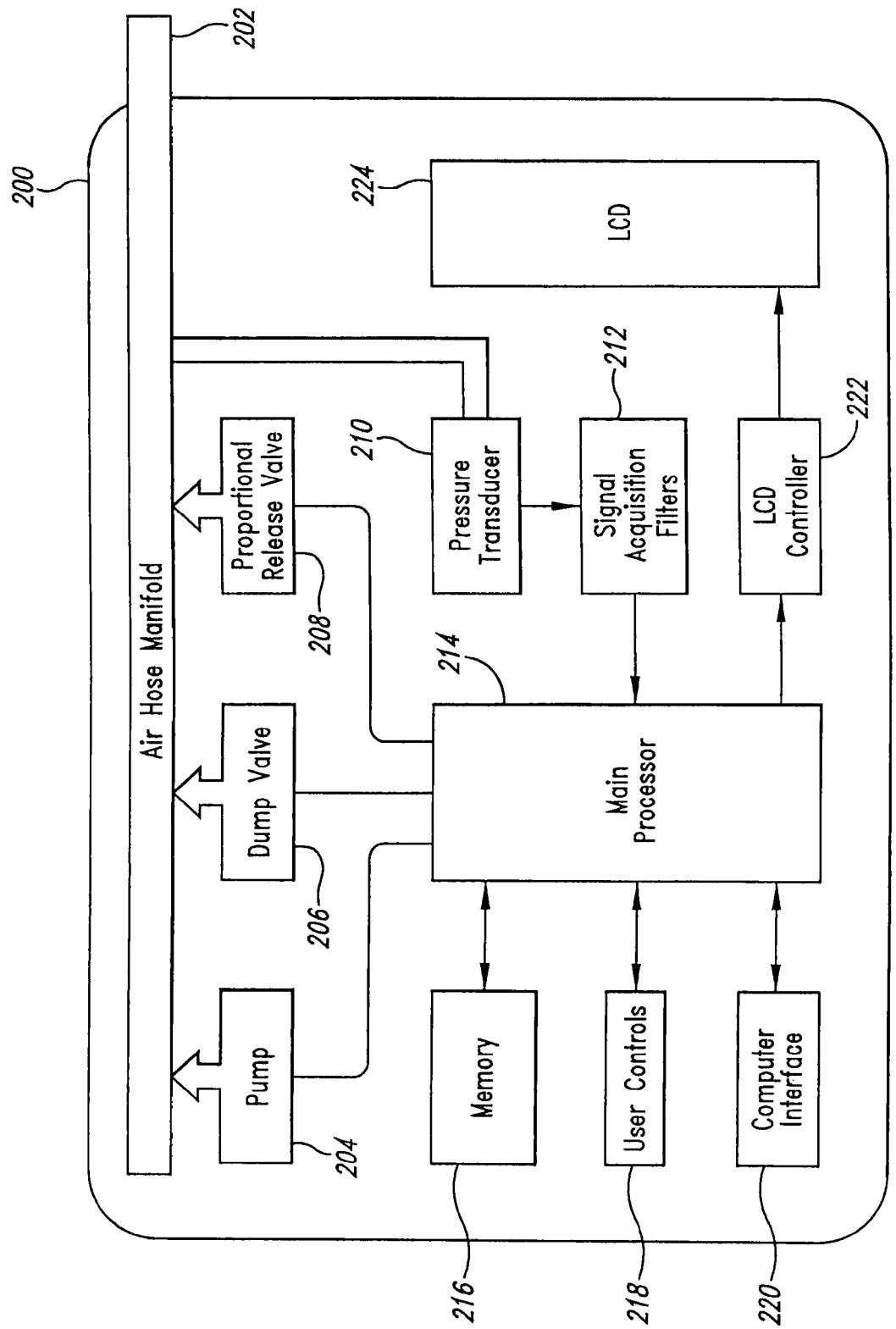
FIG. 2 shows a general block diagram of a blood pressure monitor.

FIG. 2 shows a general block diagram of a blood pressure monitor 200. The blood pressure monitor 200 has an air hose manifold 202 to connect to a pressure cuff (not shown). The blood pressure monitor 200 includes a pump 204, a dump valve 206 and a proportional release value 208, all connected to the air hose manifold 202. The pump 202 is configured to inflate the pressure cuff. The proportional release valve 208 is configured to slowly release air from the cuff.

The blood pressure monitor 200 includes a pressure transducer 210 and signal acquisition filters 212. The pressure transducer 210 is configured to measure the cuff pressure. The signal acquisition filters 220 are configured to take samples of the cuff pressure and generate oscillometric signal $x_1$ and cuff pressure signal $x_2$.

The blood pressure monitor 200 includes a processor 214 and a memory 216. The processor 214 is configured to process the oscillometric signal $x_1$ and cuff pressure signal $x_2$. The processor 214 is configured to execute instructions stored in the memory 216. In some embodiments the instructions comprise the steps describe in FIG. 1 and the discussion thereof. The memory 216 is configured to store the results of the processing.

In some embodiments, the blood pressure monitor 200 includes user controls 218 and a computer interface 220. The user controls 218 are configured to accept instructions from a user and transfer the instructions to the processor 214. The computer interface 220 is configured to transfer information between the blood pressure monitor 200 to an external computing device.

In some embodiments, the patient monitor includes a graphics controller 222 and a graphics user interface 224. The graphics user interface 224 is configured to display information retrieved from the memory 216 for the user to view. The graphics controller 222 is configured to render the information retrieved from the memory 216 into a format usable by the graphics user interface 224.

In an exemplary embodiment, a sample rate of 50 hz is used and the rank order filters use a window length of 251 points. The upper envelope is calculated using a 90th percentile rank—order filter, and the lower envelope with a 10th percentile. The $t_s$ vector has a length of 120 points and it linearly decreases from 0.6 to 0.5 as a function of the MAP (0.5 corresponding to a MAP of 60 mmHg and 0.9 to a MAP of 180 mmHg). Analogously, the $t_d$ vector has a length of 120 points and it linearly decreases from 0.95 to 0.6 as a function of the MAP (0.95 corresponding to a MAP of 60 mmHg and 0.6 to a MAP of 180 mmHg). Using vector thresholds as a function of the MAP significantly improves the accuracy of the oscillometric method. Estimating the oscillometric envelope without performing beat detection by using rank—order filters improves the robustness to motion artifact and makes the oscillometric technique more reliable. These threshold vectors can easily be generalized to multiple dimensions by including the dependence on the arm-circumference, heart rate, and other parameters. Since the dependence of the thresholds on the MAP, arm-circumference, and heart rate is conditioned on the hardware used to obtain the oscillometric and cuff pressure signals, the determination of these thresholds must be performed using a systematic optimization study where the performance of the method is monitored as these parameters are linearly varied.

Figure 3:
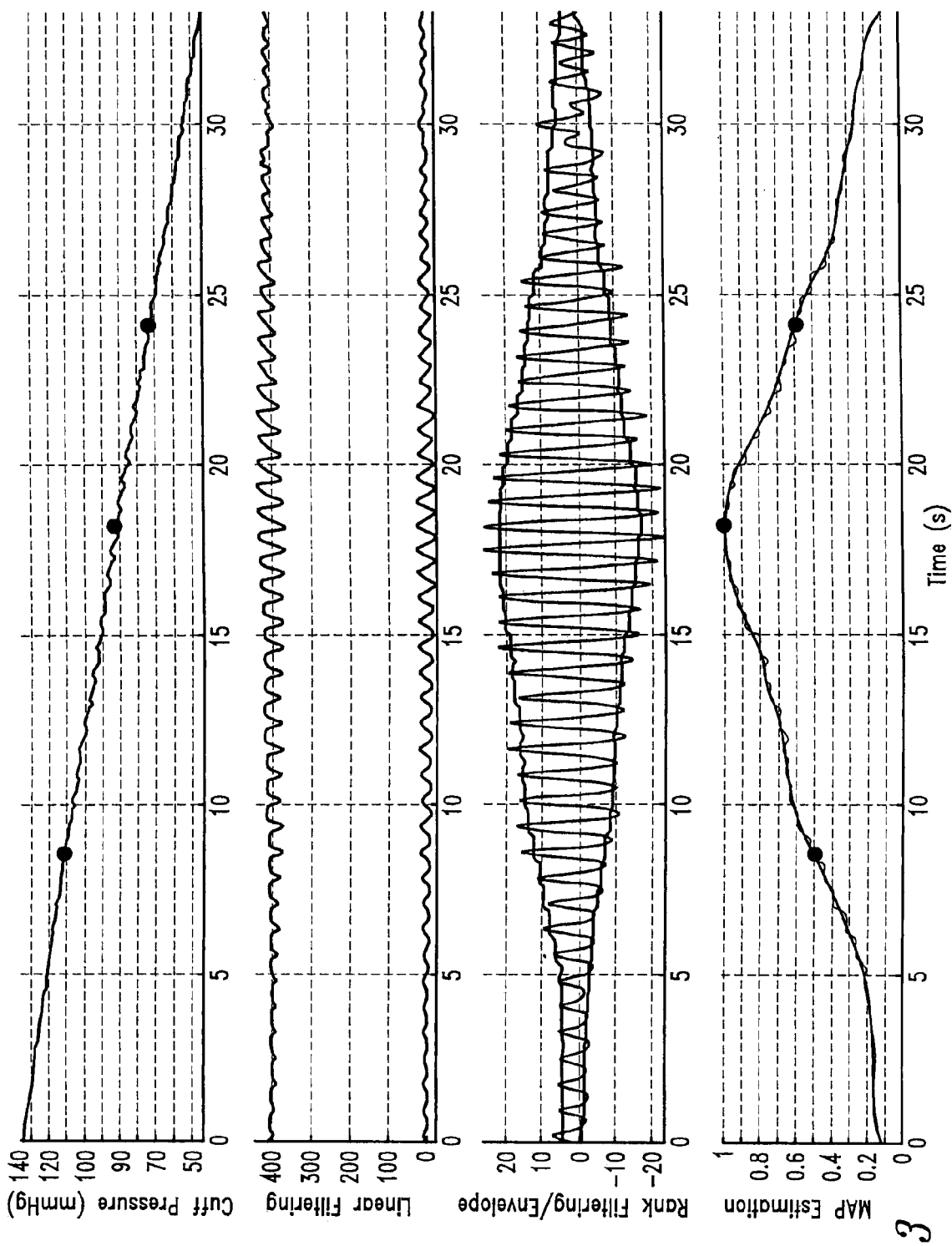
FIG. 3 illustrates the results of each method step on a normotensive patient.
Figure 4:
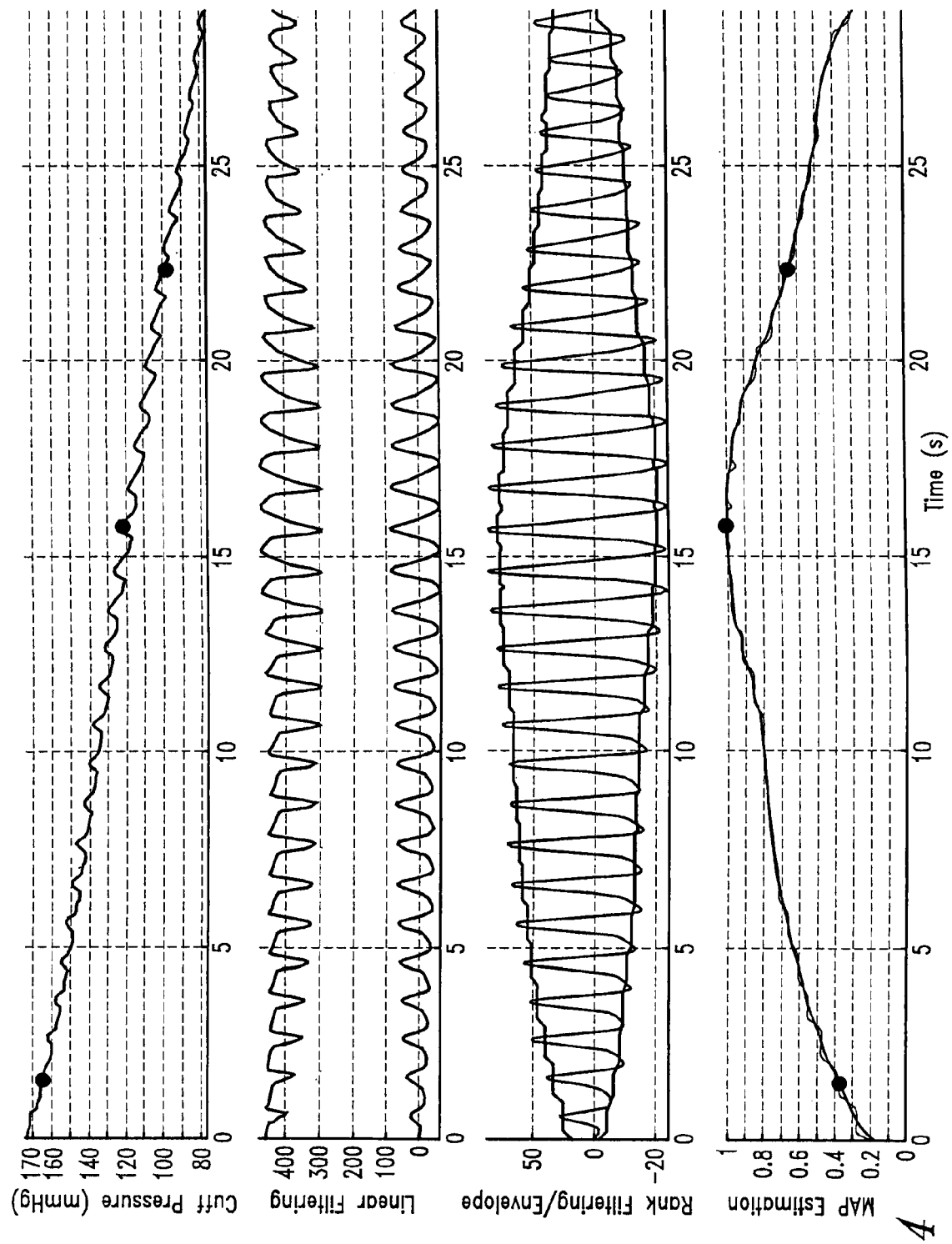
FIG. 4 illustrates the results of each method step on a hypertensive patient.
Figure 5:
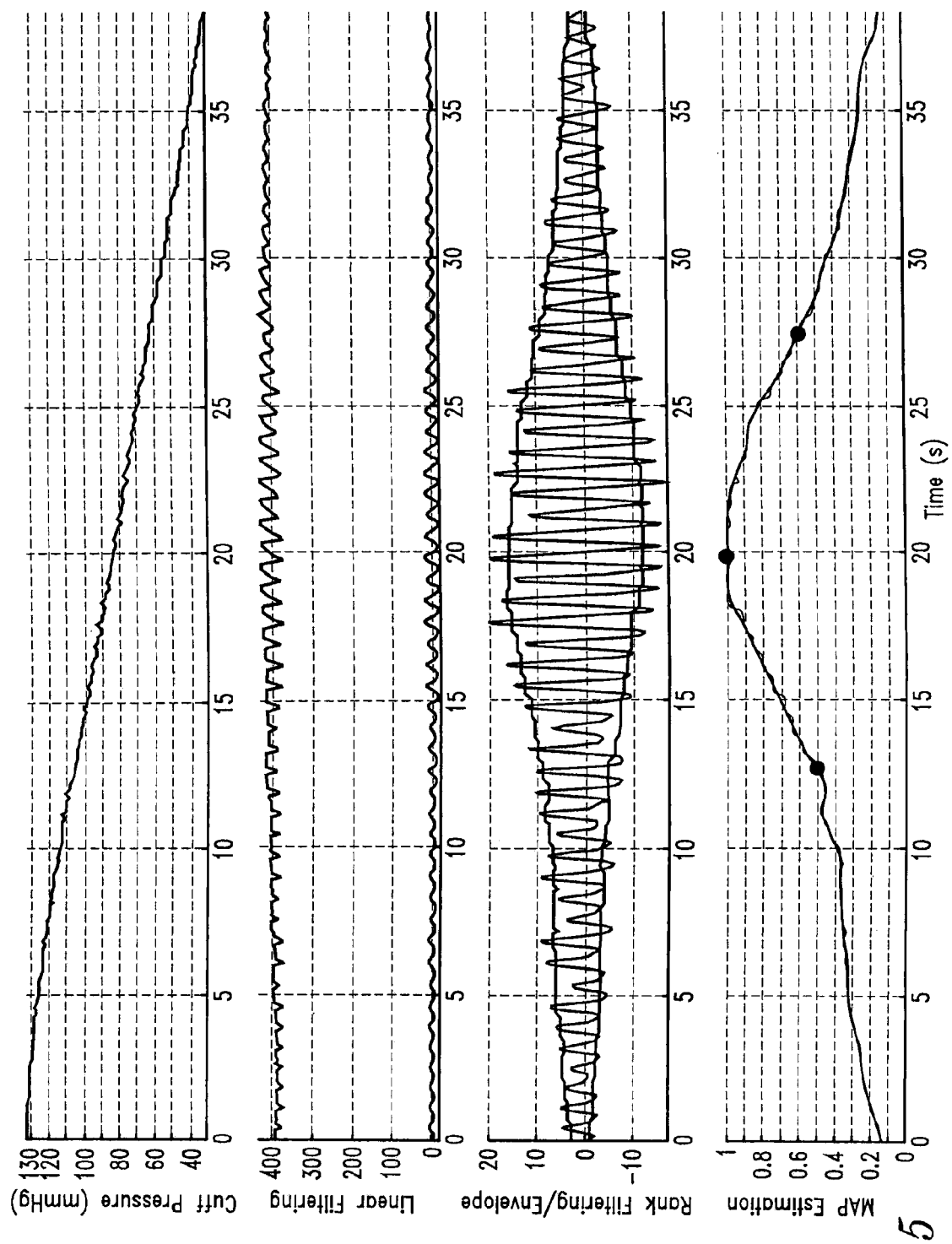
FIG. 5 illustrates the results of each method step on a hypotensive patient.
Figure 6:
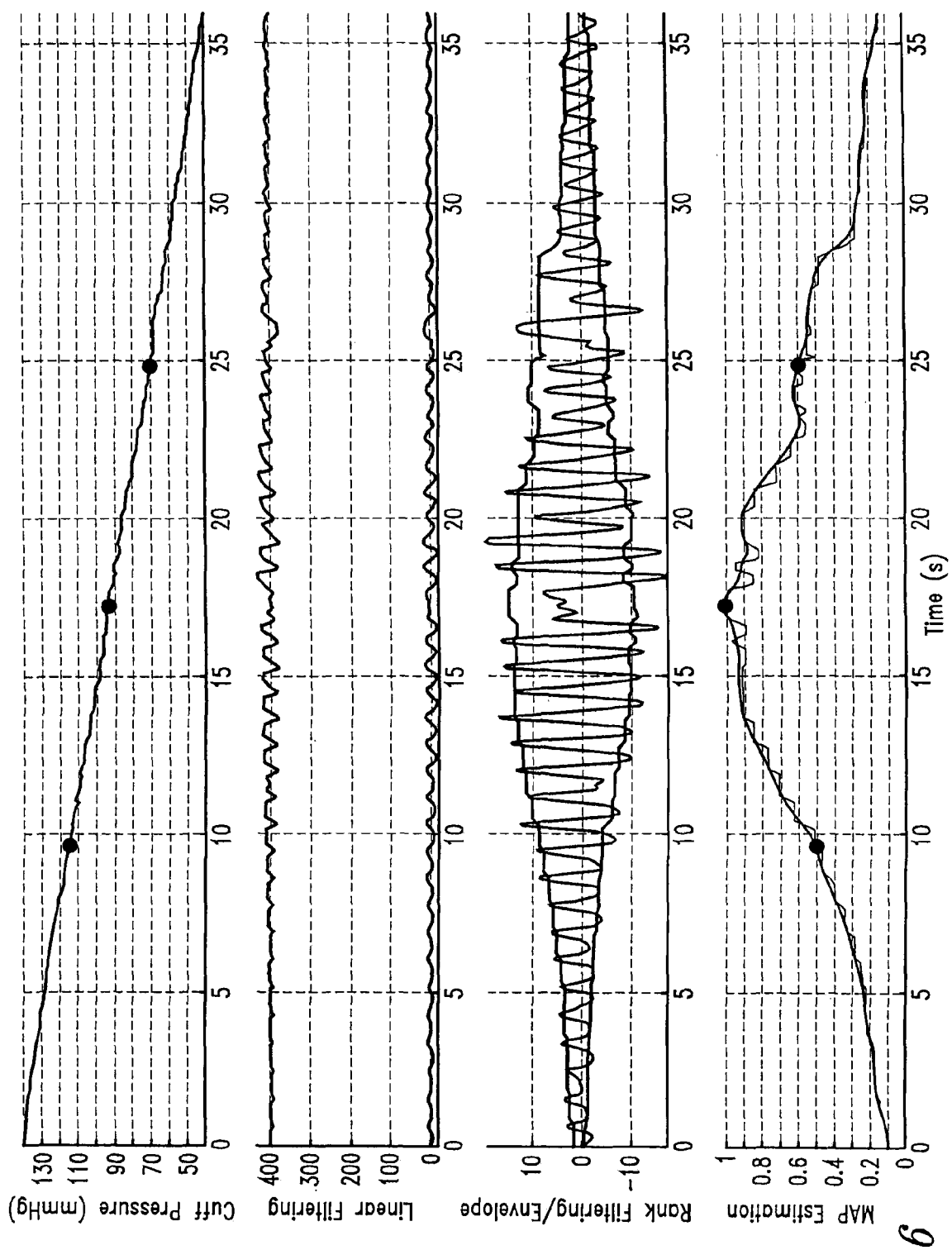
FIG. 6 illustrates the results of each method step on a patient with motion artifact.
Figure 7:
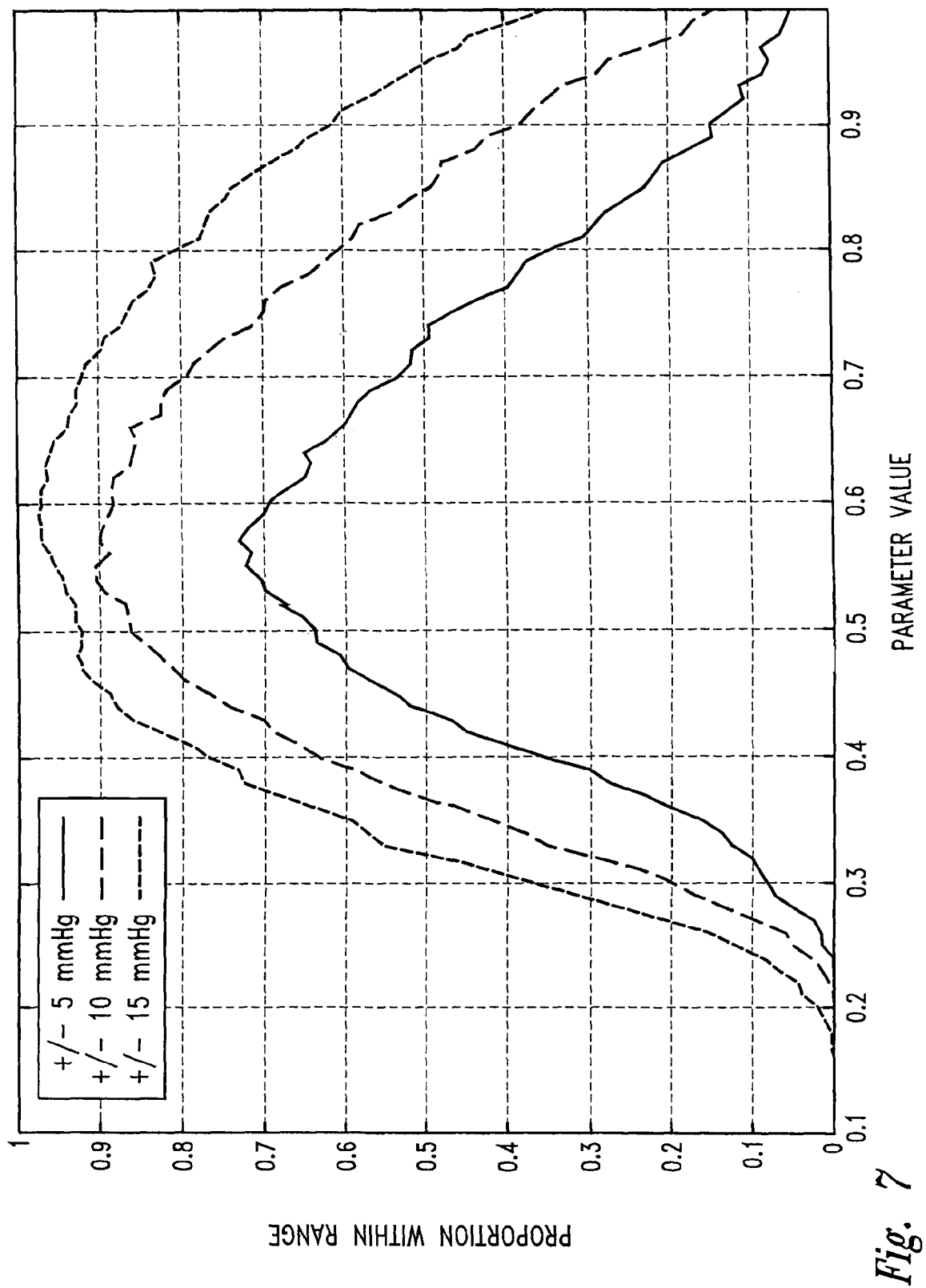
FIG. 7 shows the performance of the method as a function of the threshold value for SBP.
Figure 8:
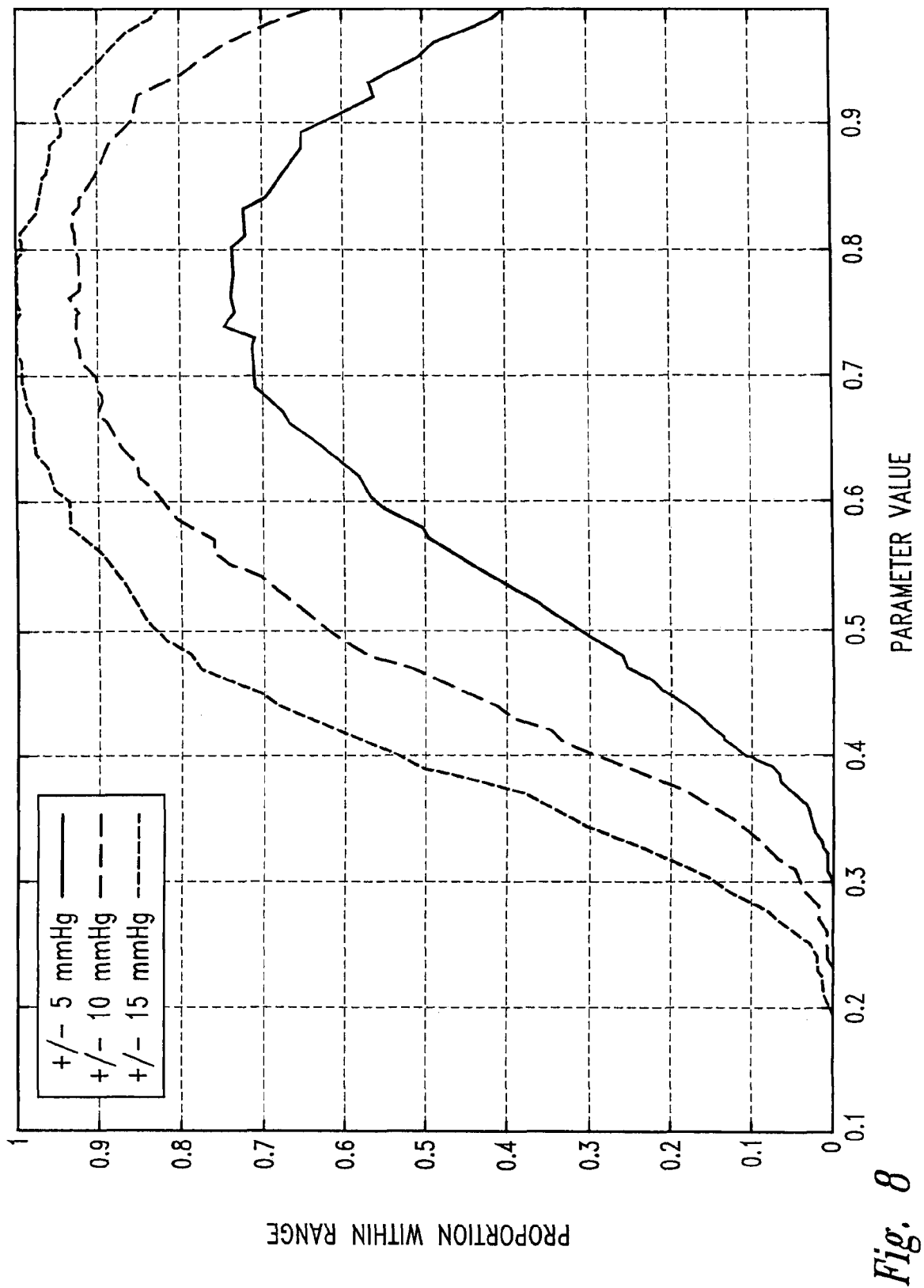
FIG. 8 shows the performance of the method as a function of the threshold value for DBP.

FIG. 3 illustrates the results of each method step on a normotensive patient. Specifically, it shows the effect of applying the lowpass and highpass filters, the estimation of the upper and lower envelopes using rank order filters, the determination of the oscillometric envelope using the difference of the upper and lower envelopes calculated using rank-order filters, the final oscillometric envelope after rank-order filtered and lowpassed filtered, and the determination of the MAP, SBP, DBP, and heart rate without beat-detection. FIG. 4 illustrates similar results for each method step on a hypertensive patient. FIG. 5 illustrates similar results for each method step on a hypotensive patient. FIG. 6 illustrates the results of each method step on a patient with motion artifact. FIG. 7 shows the performance of the method as a function of the threshold value for SBP and FIG. 8 shows the performance of the method as a function of the threshold value for DBP. These two figures also serve to illustrate the procedure to determine the single optimal threshold for SBP and DBP for a given hardware/firmware architecture. In all these plots we show the embodiment where the method is applied during linear cuff deflation. Alternative embodiments comprising the same steps are applicable to situations there noninvasive blood pressure is to be determined during cuff inflation. The method steps are the same regardless of the method of deflation (i.e. linear or step-by-step).

Figure 9:
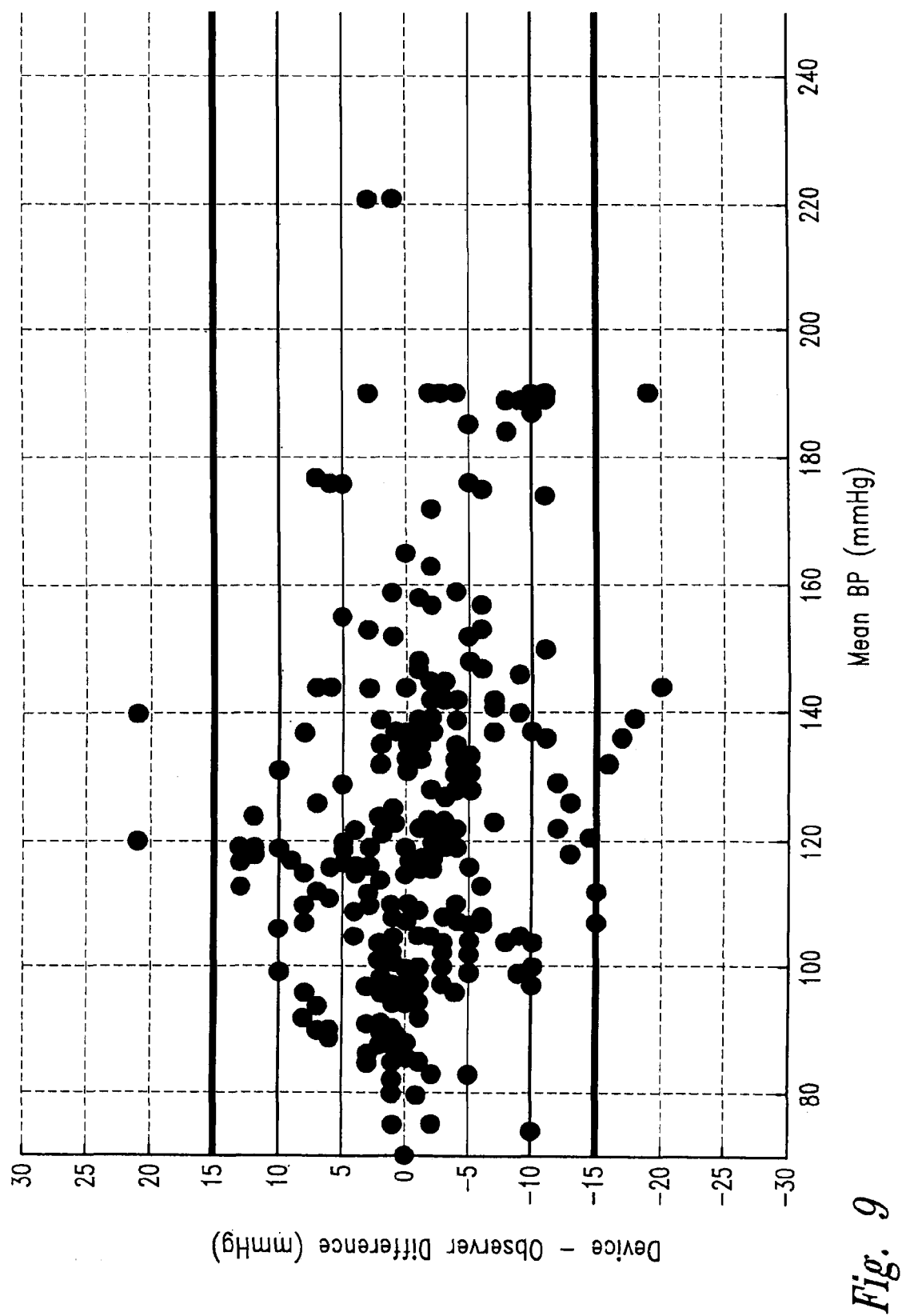
FIG. 9 shows a Bland-Altman plot illustrating the accuracy of the method for systolic blood pressure on a large patient population.
Figure 10:
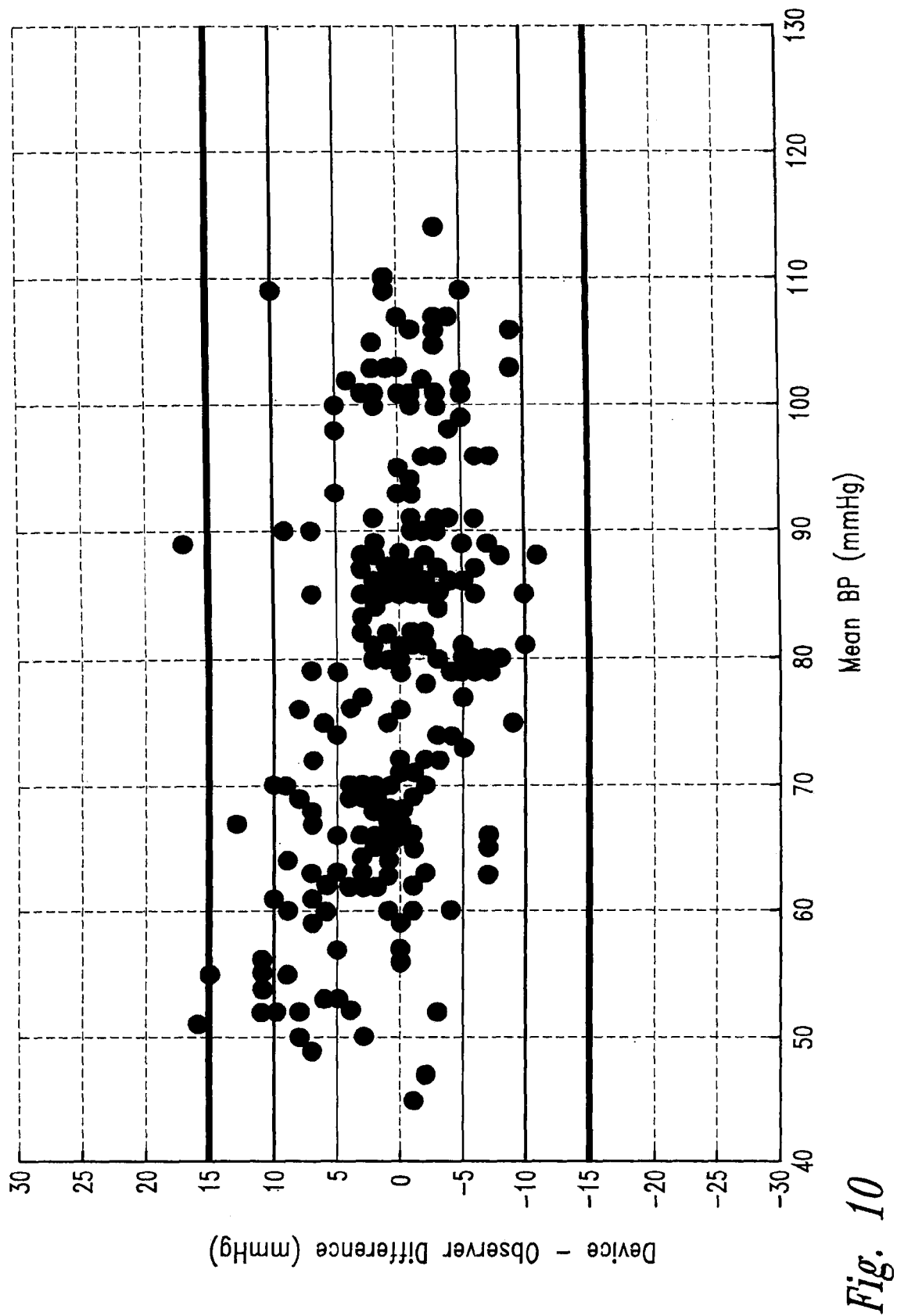
FIG. 10 shows a Bland-Altman plot illustrating the accuracy of the method for diastolic blood pressure on a large patient population.

FIG. 9 shows a Bland-Altman plot illustrating the accuracy of the method for systolic blood pressure on a large patient population and FIG. 10 shows a Bland-Altman plot illustrating the accuracy of the method for diastolic blood pressure on a large patient population.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A method for measuring non-invasive blood pressure from an oscillometric signal and a cuff pressure signal, said method implemented in a medical apparatus, comprising:
   (a) calculating a pulse pressure signal by subtracting an upper and a lower envelope of said oscillometric signal based on rank-order filters applied to said oscillometric signals; and
   (b) calculating a mean arterial pressure, a systolic blood pressure, and a diastolic blood pressure from said oscillometric signal, said cuff pressure signal, and a plurality of thresholds using a device with at least one processor.

2. The method of claim 1, wherein said oscillometric signal is filtered with one or more frequency selective filters prior to the application of said rank-order filters, and said pulse pressure signal is further filtered using a median filter and a lowpass filter to eliminate artifacts.

3. The method of claim 2, wherein calculating said mean arterial pressure is based on identifying an index value corresponding to a global maximum value in said pulse pressure signal and evaluating said cuff pressure signal at said index value.

4. The method of claim 3, wherein calculating said systolic blood pressure and said diastolic blood pressure is based on evaluating said cuff pressure signal at index values corresponding to specific percent values of said maximum value in said pulse pressure signal, said percent values specified by said thresholds.

5. The method of claim 4, wherein said plurality of thresholds are a function of the mean arterial pressure, resulting in a vector threshold with multiple scalar thresholds each corresponding to a different mean arterial pressure.

6. The method of claim 4, wherein said plurality of thresholds are a function of an arm circumference, resulting in a vector threshold with multiple scalar thresholds each corresponding to a different arm circumference.

7. The method of claim 4, wherein said plurality of thresholds are a function of a heart rate, resulting in a vector threshold with multiple scalar thresholds each corresponding to a different heart rate.

8. An apparatus for non-invasive measurement of blood pressuring, comprising:
   (a) a signal acquisition circuit to acquire a cuff pressure signal using an inflatable cuff, and to generate an oscillometric signal from said cuff pressure signal;
   (b) a memory to store said cuff pressure signal, said oscillometric signal, a plurality of processing steps; and a plurality of processing results; and
   (c) a processor configured to perform the processing steps of:
   (1) calculating a pulse pressure signal without the use of a beat detection algorithm by subtracting an upper and a lower envelope of said oscillometric signal based on rank-order filters applied to said oscillometric signals; and
   (2) calculating a mean arterial pressure, a systolic blood pressure, and a diastolic blood pressure from said oscillometric signal, said cuff pressure signal, and a plurality of thresholds; and storing the results in said memory.

9. The apparatus of claim 8, wherein (a) said upper and lower envelopes are calculated based on two rank-order filters applied to said oscillometric signal;
   (b) said oscillometric signal is filtered with one or more frequency selective filters prior to the application of said rank-order filters, and said pulse pressure signal is further filtered using a median filter and a lowpass filter to eliminate artifacts;
   (c) calculating said mean arterial pressure is based on identifying an index value corresponding to a global maximum value in said pulse pressure signal and evaluating said cuff pressure signal at said index value;
   (d) calculating said systolic blood pressure and said diastolic blood pressure is based on evaluating said cuff pressure signal at two index values corresponding to two percent values of said maximum value in said pulse pressure signal, said percent values specified by said multidimensional threshold vectors; and
   (e) said plurality of threshold vectors are a function of the mean arterial pressure, an arm circumference, and a heart rate.

* * * * *